(12) United States Patent
Schmitt

(10) Patent No.: US 10,092,681 B2
(45) Date of Patent: Oct. 9, 2018

(54) FLUID DRAINAGE CONTAINER

(71) Applicant: NUANGLE MEDICAL (PTY) LTD., Johannesburg (ZA)

(72) Inventor: Karl-Heinz Schmitt, Johannesburg (ZA)

(73) Assignee: XPELLA (PTY) LTD., Sandton (ZA)

( * ) Notice: Subject to any disclaimer, the term of this patent is extended or adjusted under 35 U.S.C. 154(b) by 330 days.

(21) Appl. No.: 14/762,605

(22) PCT Filed: Jun. 19, 2014

(86) PCT No.: PCT/ZA2014/000028
§ 371 (c)(1),
(2) Date: Jul. 22, 2015

(87) PCT Pub. No.: WO2015/003194
PCT Pub. Date: Jan. 8, 2015

(65) Prior Publication Data
US 2016/0106891 A1    Apr. 21, 2016

(30) Foreign Application Priority Data

Jun. 19, 2013 (ZA) .................................. 2013/04492
Dec. 11, 2013 (ZA) .................................. 2013/09309
(Continued)

(51) Int. Cl.
*A61M 1/00* (2006.01)

(52) U.S. Cl.
CPC ........ *A61M 1/0031* (2013.01); *A61M 1/0003* (2013.01); *A61M 1/0009* (2013.01);
(Continued)

(58) Field of Classification Search
CPC ......................... A61M 1/0003; A61M 1/0009; A61M 1/0011; A61M 1/0031; A61M 1/0068;
(Continued)

(56) References Cited

U.S. PATENT DOCUMENTS 3,018,779 A * 1/1962 Tyler ................... A61M 1/0023
417/259
3,957,052 A    5/1976 Topham
(Continued)

FOREIGN PATENT DOCUMENTS

EP    0 535 286    4/1993
GB    2 408 456    6/2005

OTHER PUBLICATIONS

International Search Report, PCT/ZA2014/000028, dated Mar. 16, 2015.

*Primary Examiner* — Adam Marcetich
(74) *Attorney, Agent, or Firm* — Young & Thompson

(57) ABSTRACT

A fluid drainage device, for use in a closed wound drainage system, which includes a fluid-receiving volume having a bore, a piston in sealing contact with the bore, a prop extending from the piston and which is connected to an energy storage device, wherein the piston can be user-actuated between a first position, whereby energy is stored in the energy storage device, to a second position, whereby energy is released from the energy storage device, to increase the size and reduce the pressure of the volume, allowing fluid to flow from a conduit into the volume.

16 Claims, 10 Drawing Sheets

(30) Foreign Application Priority Data

Apr. 2, 2014 (ZA) .................................. 2014/02400
May 12, 2014 (ZA) .................................. 2014/03355

(52) U.S. Cl.
CPC ........ *A61M 1/0011* (2013.01); *A61M 1/0068* (2014.02); *A61M 2205/073* (2013.01); *A61M 2205/3337* (2013.01)

(58) Field of Classification Search
CPC .... A61M 2205/073; A61M 2205/3337; A61M 1/0005; A61M 1/007; A61M 1/06; A61M 2005/3143
See application file for complete search history.

(56) References Cited

U.S. PATENT DOCUMENTS

| | | | | |
|---|---|---|---|---|
| 4,397,643 A | * | 8/1983 | Rygiel | ................ A61M 1/0015 215/11.3 |
| 4,404,924 A | | 9/1983 | Goldberg et al. | |
| 4,578,060 A | * | 3/1986 | Huck | ................... A61M 1/0011 604/133 |
| 4,981,474 A | * | 1/1991 | Bopp | ................... A61M 1/0011 600/580 |
| 4,997,420 A | * | 3/1991 | LeFevre | ................ A61M 5/145 128/DIG. 12 |
| 5,017,190 A | * | 5/1991 | Simon | ............... A61M 5/31551 604/110 |
| 5,071,409 A | * | 12/1991 | Rosenberg | .......... A61M 1/0009 600/579 |
| 5,800,405 A | * | 9/1998 | McPhee | .............. A61M 5/1454 604/135 |
| 6,213,985 B1 | * | 4/2001 | Niedospial, Jr. | .... A61M 5/3129 604/187 |
| 6,352,673 B1 | * | 3/2002 | Rainin | ................. B01L 3/0217 422/525 |
| 6,613,024 B1 | * | 9/2003 | Gargione | ............. A61M 5/315 604/218 |
| 2004/0054332 A1 | * | 3/2004 | Ferguson | ............ A61M 5/3129 604/220 |
| 2005/0002810 A1 | * | 1/2005 | Gould | ................ F04B 43/0063 417/472 |
| 2008/0143107 A1 | * | 6/2008 | Bowling | .............. F16L 19/005 285/334.5 |
| 2008/0312640 A1 | * | 12/2008 | Grant | .................... A61M 39/10 604/533 |
| 2009/0209823 A1 | * | 8/2009 | Yamane | ................ A61B 1/015 600/158 |
| 2009/0270843 A1 | | 10/2009 | Saxena et al. | |
| 2010/0228205 A1 | * | 9/2010 | Hu | ...................... A61M 1/0037 604/319 |
| 2012/0071845 A1 | * | 3/2012 | Hu | ...................... A61M 1/0066 604/319 |
| 2012/0302964 A1 | * | 11/2012 | MacDonald | ........ A61M 5/3155 604/189 |
| 2013/0041351 A1 | | 2/2013 | Shahim | |

* cited by examiner

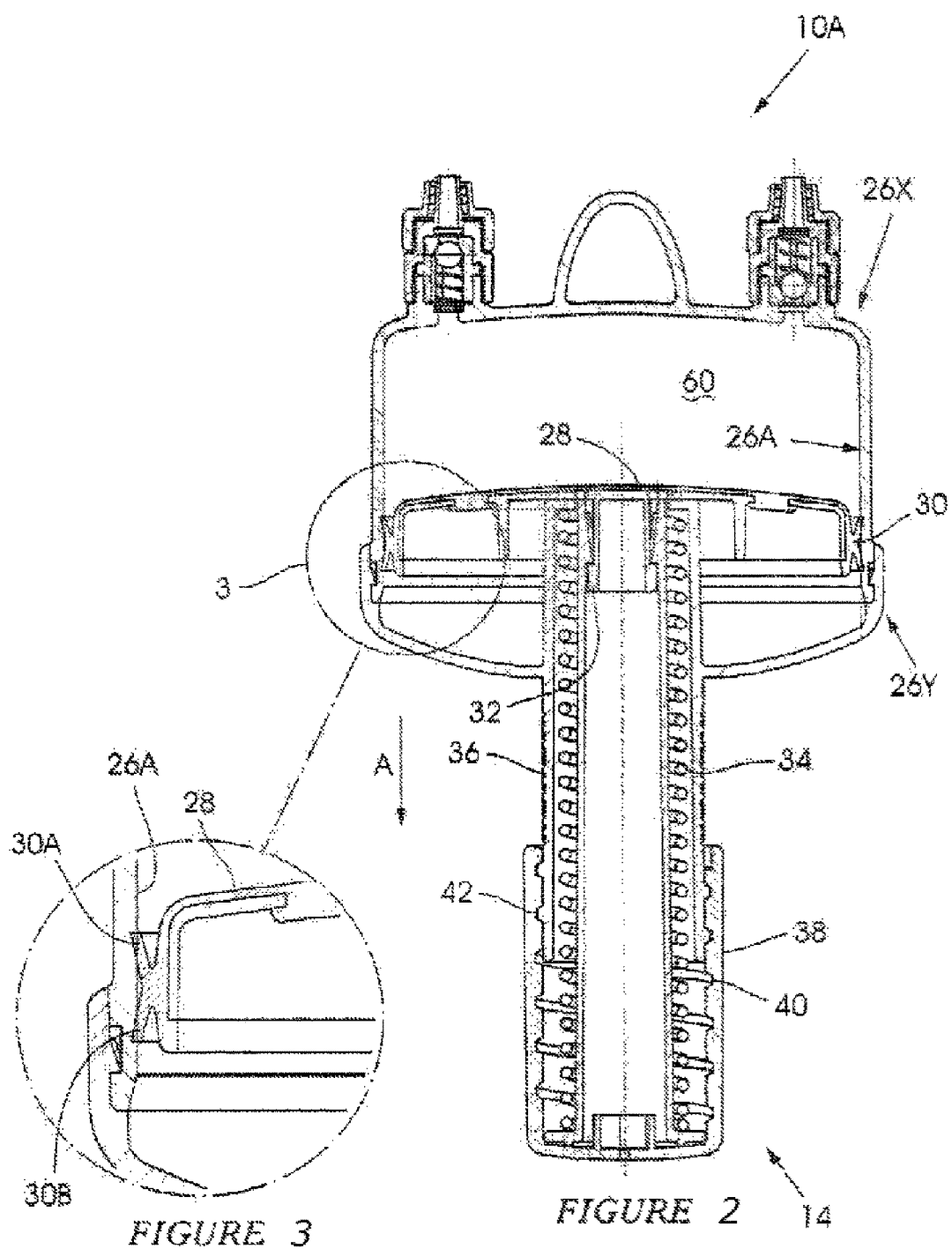

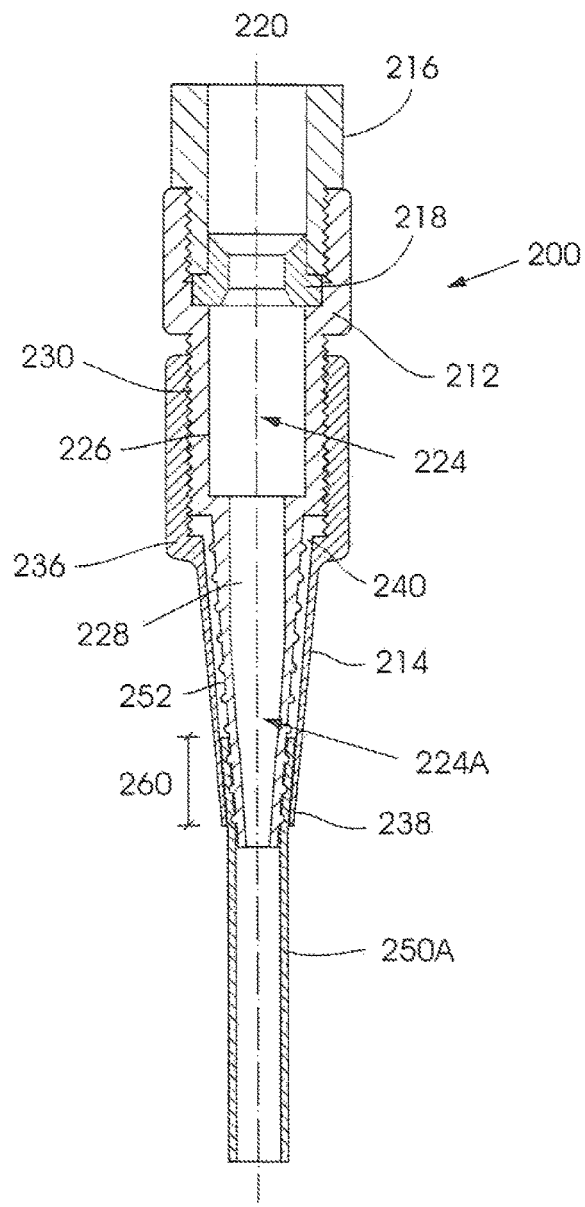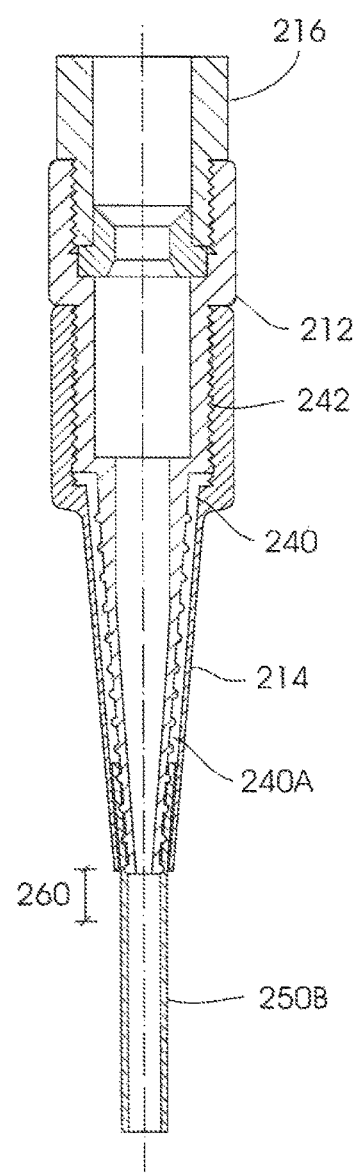
FIGURE 10
FIGURE 11

FLUID DRAINAGE CONTAINER

BACKGROUND OF THE INVENTION

This invention relates to the drainage of body fluids from a closed wound.

The draining of fluid from a closed wound, particularly after surgery, is beneficial as it promotes healing and removes a build-up of fluid which would other otherwise remain in the body and which would increase the chances of infection.

Various drainage systems have been proposed most of which operate through the use of a partial vacuum in order to promote the drainage of fluids. These drainage systems are usually in the form of compressive containers, electric vacuum machines or pre-charged disposable containers.

Although these systems all drain fluid, they have varying degrees of efficacy and the manufacturing cost thereof can often be high. In some devices, a vacuum is not always constantly applied and a user must constantly check and re-adjust the device to ensure that the fluid is being drained effectively. Typically, the vacuum level is higher at the start of a working cycle of a device and lower at the end of the working cycle. This variation affects the fluid drainage rate. Some devices are also specific to the volume of fluid to be drained and it is often not possible to adjust this volume easily to suit a particular patient's needs.

An object of the present invention is to provide a fluid drainage device, suited for use with a closed wound drainage system, which is cost effective to manufacture and which at least partially addresses the aforementioned issues.

SUMMARY OF THE INVENTION

The invention provides a fluid drainage device for use in a closed wound drainage system which includes a body with a cylindrical bore which defines at least part of a fluid-receiving volume, an inlet to the fluid-receiving volume, a piston in sealing contact with the bore which partly bounds the fluid-receiving volume inside the bore, the piston being movable between a first position and a second position, a piston rod which extends from the piston, an energy storage device engaged with the piston rod, a user-actuated handle mechanism which is movable relative to the body in a first direction, to allow the piston to move from the first position, whereby energy is stored in the energy storage device, to the second position, whereby energy is released from the energy storage device, thereby increasing the size of the fluid-receiving volume, reducing the pressure in the fluid-receiving volume and allowing fluid to flow from a suitable conduit through the inlet and into the fluid-receiving volume.

The energy storage device may be compression spring.

Preferably the spring constant of the compression spring is relatively invariable during movement of the piston between the first and second positions.

Preferably the spring is formed from steel that is electro galvanized and blue passivated to prevent rust.

The handle mechanism may include at least one threaded component which is movable to allow the energy storage device to be loaded with, or to release, energy.

Preferably the handle mechanism includes an inner tubular member which is externally threaded and in which the piston rod and energy storage device are housed and an outer tubular member which is threadedly engaged with the inner tubular member such that rotation of the outer tubular member in a first direction causes the outer tubular member to move linearly along the inner tubular member, causing the energy storage device to release energy, thereby creating a vacuum or a region of reduced pressure and causing or allowing the piston to move to the second position.

The handle mechanism may include indicating means, e.g. on a periphery thereof, to indicate the volume of fluid to be drained.

As the fluid enters the fluid-receiving volume, the pressure in the fluid-receiving volume increases. The suction effect, exerted via this volume, thus decreases and ultimately a stage is reached, as determined by the setting of the indicating means, at which the fluid is no longer drawn through the inlet into the fluid receiving volume.

In one form of the invention the inlet valve is a one-way valve, and the device has an outlet valve to allow the fluid in the fluid-receiving volume to be drained.

The device may be formed from clear plastics material of any suitable kind.

The device may include a formation to allow the body to be suspended from an overhead structure.

In a preferred embodiment of the invention the piston is movable in the bore against a frictional force which is at a maximum value at the beginning of a working stroke of the piston and which is at a minimum value at an end of the working stroke of the piston and which decreases as the piston moves over its working stroke from the maximum value to the minimum value.

The variation in the frictional force may be achieved in any appropriate way. The invention is not limited in this respect. However, in one approach, the shape of the bore is varied so that the frictional force reduces from the beginning of the working stroke towards an end of the working stroke. This may be achieved by increasing the cross-sectional area of the bore, preferably on a linear basis, from one end of the bore to an opposing end. Additionally, use may be made of an appropriate seal which is fitted to the piston and which provides a sealing interface between the piston and an opposing surface of the bore despite the change in dimension of the bore.

In the device as described, an inlet to the volume, and an outlet from the volume, are positioned on the body at appropriate locations. Typically spring-loaded values are fixed to the inlet and outlet respectively. The outlet, which functions as a drain from the volume, has a relatively weak spring which acts on the valve. A difficulty which has been encountered is that, in use, the drain valve does not always seal properly. On the other hand the force exerted by the spring on the inlet valve can influence the vacuum which is induced in the volume. Variations in the vacuum affect the repeatability of operation of the drainage function.

To address this problem, in one embodiment of the invention a single opening (inlet/outlet) is formed in the body to the fluid receiving volume. A valve, of compound construction, is connected to the opening. The valve has an inlet port and a drain port and is operable to connect the inlet port to the opening, and hence to the fluid receiving volume, so that the device can act in a drainage mode. Alternatively, the valve is operable to connect the drain port to the opening so that fluid from the fluid receiving volume can be expelled to waste, when required.

The compound valve preferably manually actuable and is movable, e.g. rotatable, between a first limiting position at which the opening is connected to the inlet port and a second limiting position at which the opening is connected to the drain port.

In use, the fluid drainage device is connected to a tube which extends from a wound to a receptacle i.e. the container body, in to which fluid is drained. It should be possible, with ease, to connect the body to a tube which could have one of a number of different sizes. This particular problem can be overcome by preselecting tubes of appropriate sizes or by making use of adaptors developed for the purpose. This however, is not necessarily an ideal approach for it can be time-consuming to implement and, additionally, a stock holding of tubes or adaptors of various sizes etc. must be established.

This aspect can be addressed by providing a connector for use with the fluid drainage device which includes a first tubular member with a first section of constant external circular cross-section which is externally threaded and a second section which extends from the first section and which is tapered reducing in external size away from the first section, and a second tubular member with an internal passage, which has a first part where the passage has a constant cross-sectional area and is internally threaded so that the first part is threadedly engageable with the first section, and a second part which encloses a length of the passage which is tapered reducing in cross-sectional area moving away from the first part.

The degree of taper of the second section may be substantially the same as the degree of taper of the passage enclosed in the second part.

The first tubular member may be attached to the second tubular member by inserting the second section through the passage within the first part so that the second section then extends into the tapered passage in the second part. The first part may then be threadedly engaged with the first section.

As the first part is further threaded onto the first section, the second section is caused to enter to a greater extent into the tapered passage of the second part.

With the tubular members interengaged as described a gap is formed between opposing surfaces of the second section and of the second part. This gap, in cross-section, is annular and, viewed from one side, is tapered i.e. the gap generally conical in shape. The width of the annular gap, formed between opposing surfaces of the second section and the second part, is reduced as the first part is further threaded onto the first section.

The first and second tubular members are preferably made from a plastics material. A requirement in this respect is that it should be possible, with relative ease, to sever the second section at an appropriate location and the second part at an appropriate location. This is done taking into account the size of a tube (internal diameter and external diameter) which is to be coupled to the connector.

The connector suited for use with the fluid drainage device but its application is not limited to this specific implementation.

BRIEF DESCRIPTION OF THE DRAWINGS

The invention is further described by way of examples with reference to the accompanying drawing in which:

FIG. 2 is similar to FIG. 1 but illustrating another fluid drainage device according to the invention;

FIG. 3 is a view on an enlarged scale and in cross-section of a portion of the device shown in FIG. 2;

FIGS. 10, 11, 12 and 13 respectively illustrate in cross-section and from one side a connector, which forms part of a preferred embodiment of a drainage device according to the invention, but wherein the connector is coupled to a flexible pipe or conduit which increases in diameter from FIG. 10 to FIG. 13 respectively.

DESCRIPTION OF PREFERRED EMBODIMENTS

Figure 1:
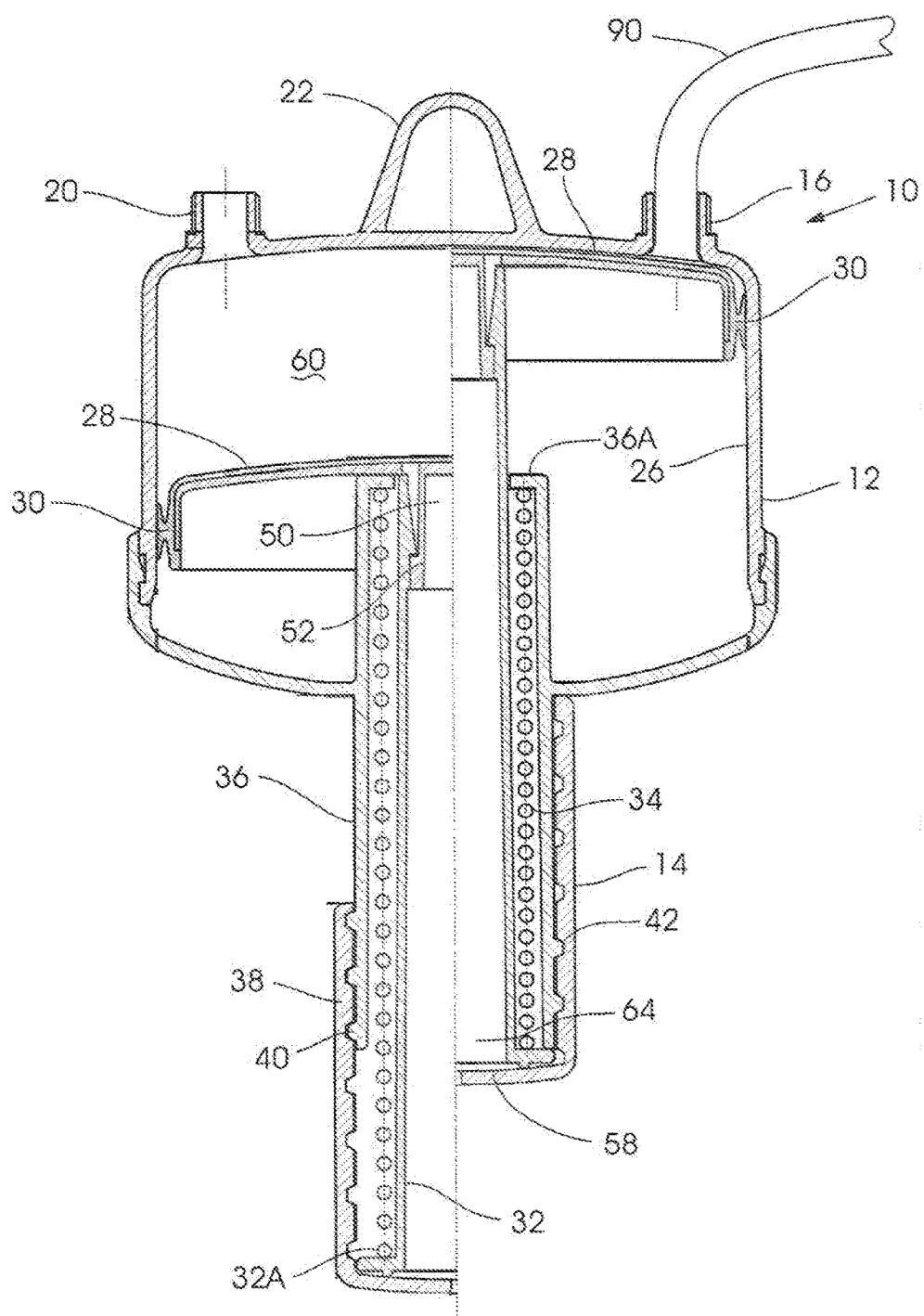
FIG. 1 shows a fluid drainage device according to one form of the invention, from one side and in cross-section— the right side thereof showing a piston inside a container body in a first position and the left side showing the piston in a second position inside a bore of the container body.

FIG. 1 of the accompanying drawings shows a device 10 for use a fluid drainage system. The device has a container body 12 and a user-actuable handle mechanism 14 at a lower end of the body. A fluid inlet 16 is positioned on one side of a lid 18. A fluid drainage outlet 20 is positioned on an opposing side of the lid.

A formation 22 which allows the container body 12 to be suspended from overhead structure, not shown, is centrally located on the lid.

The right and left ides of the drawing how the device 10 in cross section in different operative modes.

The body 12 is cylindrical in shape and, internally, defines a cylindrical bore 26 with a smooth internal surface. A piston 28, of complementary shape to the bore, is slidingly positioned inside the bore. The piston has an external seal 30 which ensures that an intimate seal established between the piston and the bore. A fluid-receiving volume 60 of variable size is defined by the position of the piston inside the bore.

A piston rod 32 projects from the piston 28. An energy storage device 34, shown here in the form of a compression spring, is engaged with the piston rod.

The handle mechanism 14 comprises an inner tubular member 36, fixed to the body, which is threadedly engaged with an outer tubular member 38 which is rotatable in relation to the inner tubular member. In order to achieve this, the inner tubular member has external threads 40 and the outer tubular member has internal threads 42 which are engaged with the threads 40.

An end 50 of the piston rod 32 bears against and is connected to the piston and is held in place by complement formations 52 on the inner tubular member.

The spring 34 is housed within the user actuable handle mechanism. It reacts against an end 36A of the ember 36 and exerts a force on an end 32A of the rod 32 which urges the piston 28 in a direction A, shown on the left side of FIG. 1.

The inner tubular member 36 is held captive to the outer tubular member 38 through interengagement of the threads 40 and 42. When the outer tubular member is fully threaded into the inner tubular member as shown in the right side of FIG. 1, an end surface 58 thereof abuts an end surface 64 of the inner tubular member.

In use, an elongate flexible drainage conduit 90, shown on the right side of FIG. 1, is connected to the inlet 16. A free end of the conduit is positioned, as is known in the art, in a body cavity from which fluid is to be drained (not shown). At this stage the outer tubular member 38 is fully engaged with the inner tubular member and the spring 34 is loaded with energy. The piston 28 is in the first position shown on the right side of FIG. 1 and the volume 60 has a minimum value.

Upon rotation in a first direction relative to the inner member 36, the outer tubular member 38 rides over the threads 40 and moves in an axial direction away from the body 12. The handle 14 is then in an extended configuration as shown in the left side of FIG. 1 and, as a consequence, the spring 34 releases energy thereby pulling the piston 28 away from the lid 18 towards a base of the container body.

Indicating markings 62 are provided on an outer surface of the inner member 36. The markings show the volume of fluid to be drained. This volume can be adjusted by appropriately rotating the outer member 38. Once quantity of fluid has been drained, corresponding to the indicated volume, the piston 28 will have moved to a position determined by the position of the member 38 and the pressure in the volume 60 will have increased atmospheric pressure. The drainage of fluid into the volume 60 then stops.

During the aforementioned process the volume 60 is increased in size.

The spring 34 is designed to have a relatively invariable spring constant as the piston moves between extended and compressed positions.

Fluid in the volume 60 can be drained by rotating the outer member 38 in a direction which is opposite to the first direction, thereby loading the spring 34 and causing the piston 28 to push the fluid through the outlet valve 20 so that it can be discarded.

The fluid inlet 16 and the fluid outlet 2 can be sealed by means of suitable caps, not shown.

As the connections to, and in, the container body are essentially airtight the volume increase translates into a reduction in the pressure prevailing in the volume to a level which is slightly below atmospheric pressure. Fluid in the body cavity is then expelled by atmospheric pressure actors into the conduit 90 and flows into the volume 60 where it is collected.

The container body can be made from an appropriate transparent material so that a visual indication is available to a user of the content of the volume.

FIG. 2 illustrates a device 10A which is substantially the same as the device 10. For this reason reference numerals which are the same as reference numerals used in FIG. 1 are used to designate like components in FIG. 2.

The vacuum in the volume 60 is at a level at the start of a working stroke and reduces over the length of the working stroke. At the start of the working stroke the force exerted by the spring 34 is at a maximum and the spring compressed to a maximum extent. The volume 60 is then of a minimum size. The degree of compression of the spring reduces over the working cycle and the volume 60 increases in size.

The device 10A of FIG. 2 uses a seal 30 which has lips 30A and 30B i.e. it is a double-lip hydraulic seal made from a suitable plastics material such as polyurethane. The lips 30A and 30B, in the circular cylindrical bore 26, exert uniform pressure on a surface 26A of the bore. In FIG. 3 the lips 30A and 30B are shown in an uncompressed form.

In order to achieve a variable friction force between the piston and the bore, the bore is slightly tapered and increases in cross-sectional dimensions from one end 26X to an opposing end 26Y. The degree of taper is slight, typically of the order of 0.2 mm or 0.3 mm. Although the cross-sectional size of the bore increases the flexible double-lip seal is able to accommodate the dimensional change and exhibits a good sealing characteristic over the length of the piston working stroke.

With the seal in the region 26X a frictional force between the piston and the cylinder is relatively high due to the lower tolerance between these components. When the piston is in the region 26Y there is a bigger gap between the piston and the surface 26A and thus the frictional force between the seal and the cylinder decreases.

By way of example if the bore of the cylinder is circular cylindrical and uniform then the friction throughout a working stroke is uniform. Calculations and tests have shown that the vacuum level at the end of a working stroke would be approximately 70% of the vacuum level at the beginning of the working stroke. By tapering the bore, in the manner described, the change in the vacuum level from the maximum to the minimum is reduced to about 7%. This means that the rate at which fluid is drained from a body cavity by the device 10A is kept substantially constant over the working stroke of the device.

FIGS. 4 to 9 show a device 10B which is substantially the same as the device 10. However, the fluid inlet 16 and the fluid drainage outlet 20 shown in FIG. 1 are dispensed with and are replaced by a single opening 100 to which is fitted a compound, or multiport valve 102 which has a circular base 104, a circular disc seal 106 and a circular cover 108.

The base 104 has an aperture 110 which is directly and permanently connected to the opening 100. Additionally the circular base 104 has an inlet port 112 and a drain port 114.

Figure 4:
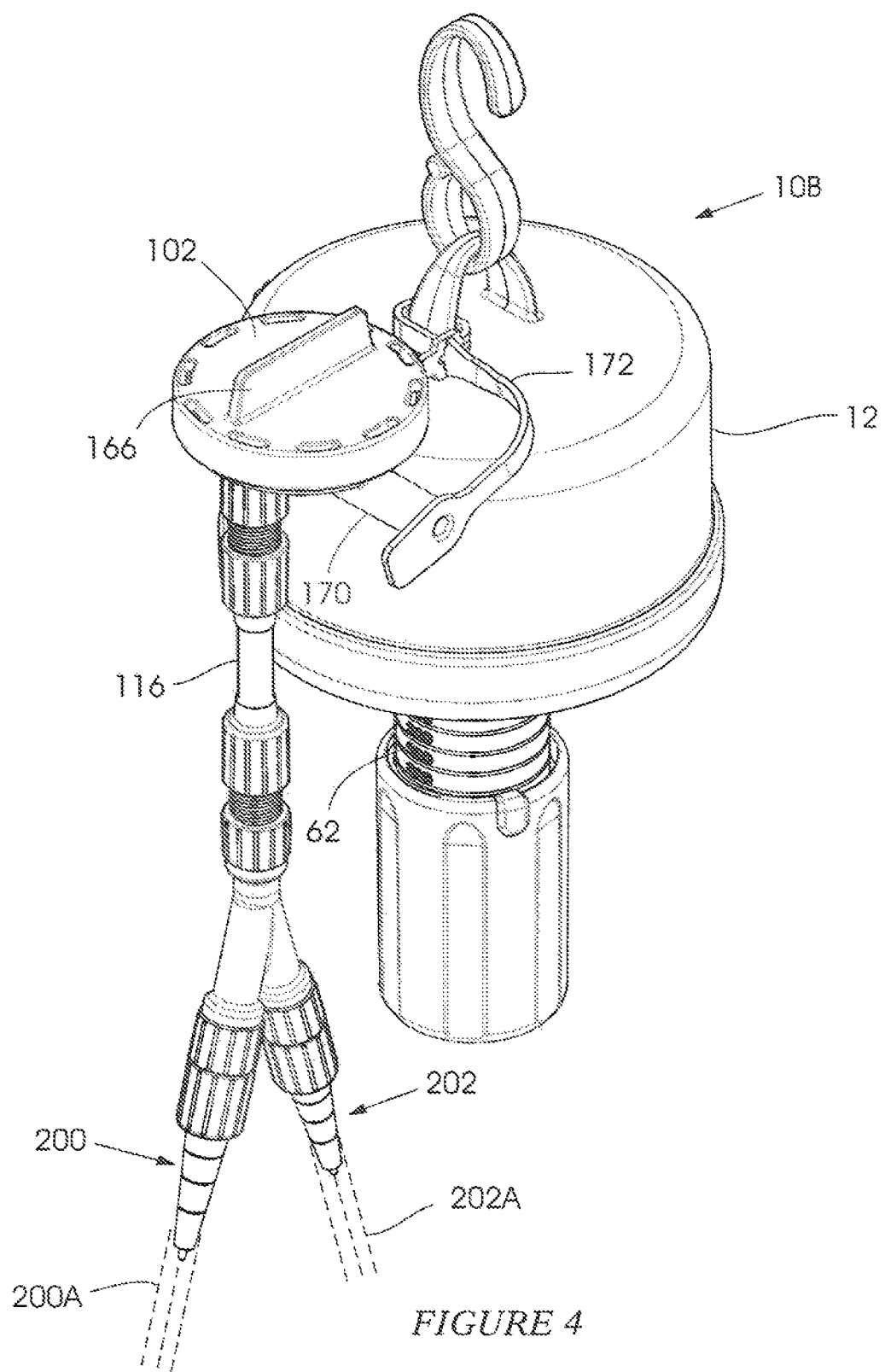
FIG. 4 is a perspective view of a modified drainage device according the invention with a multiport or compound valve in a first position.
Figure 5:
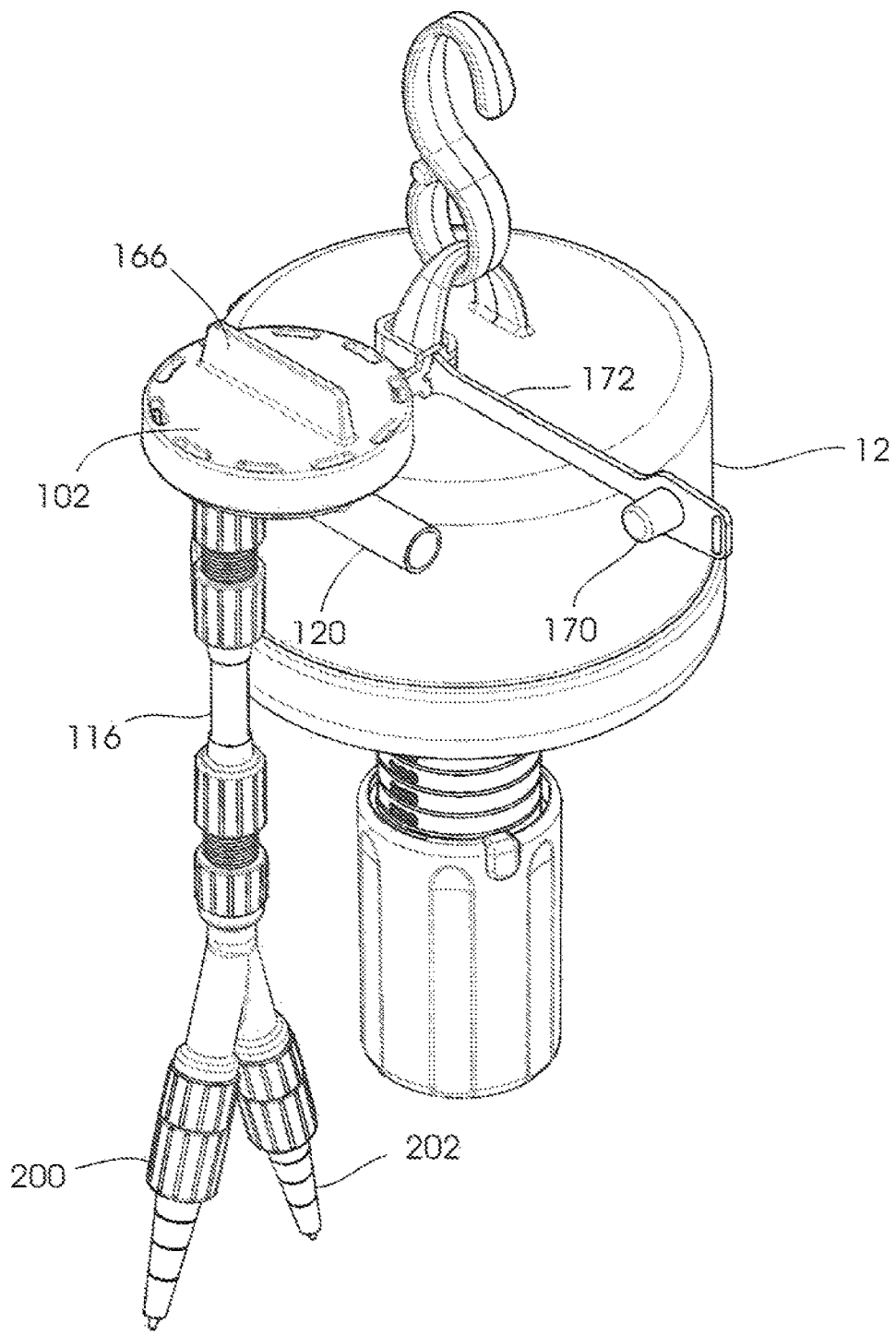
FIG. 5 is similar to FIG. 4 but with the valve in a second position.
Figure 6:
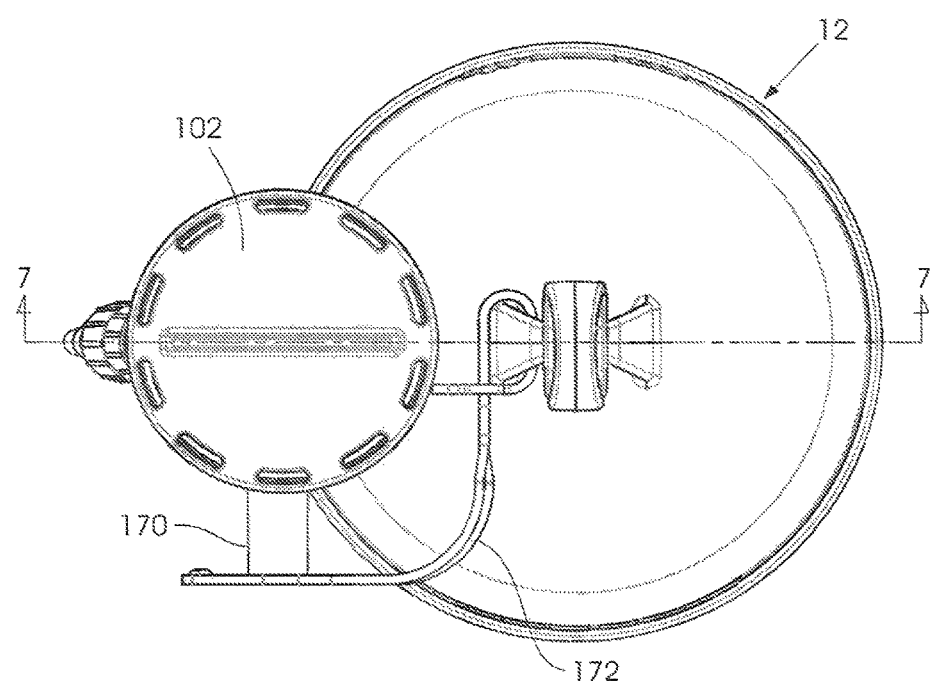
FIG. 6 is a plan view of the drainage device in FIG. 4.

The inlet port 112, in use, is connected to a flexible drainage tube 116, as is shown in FIGS. 4 and 5, in accordance with requirements known in the art. This aspect is not further described herein. The drain port 114 leads to a short tube 120 which extends to one side of the base.

The disc seal 106 is made from rubber and is engageable with a tight fit with the circular base whereby, to some extent at least, the seal is surrounded by a wall 104A of the base. On a lower side 124, shown in FIG. 9, the disc seal has an arcuate groove 130 which extends through about 180°. The groove is surrounded by a raised bead 132 which, in use, provides a sealing interface between the disc seal 106 and an inner surface 134 of the circular base 104.

On an upper side 140 the disc seal has a number of openings 142 which are uniquely engageable with corresponding spigots 144 which project from an inner surface 146 of the cover 108. Additionally the cover has a plurality of formations 150 on an inner surface of a wall 152 (see FIG. 9). These formations are engageable with complementary formations 160 on the wall 104A. The arrangement is such that the disc seal is only engageable in a predetermined orientation with the cover 108 and, in turn, the cover is only engageable in a predetermined orientation with the circular base 104.

The cover 108 has a raised handle 1 on an upper surface which facilitates manual operation of the valve.

The device 108 is used substantially the same way as what has been described hereinbefore. The flexible drainage pipe 116 is connected to the inlet port 112. When the cover 108 is turned in an anticlockwise direction to a limiting position the groove 130 is positioned so that the net port is connected to the opening 100 and fluid drainage can then take place in a conventional manner. The drain port 114 sealed from the port 110 and the port 112 by the seal which is created by the bead 132 bearing on the surface 134.

If the cover 108 is manually rotated in a clockwise direction through 90° then a limiting position is again reached but, in this instance, the drain port is connected to the port 110 i.e. to the volume through the opening 100, and the net port is sealed by the bead 132. Fluid can now be expelled from the volume 60 to waste.

FIGS. 4 and 5 illustrate a plug 170 which is attached to a flexible tie 172 secured to the body 12. In FIG. 5 the plug is displaced from the tube 120. In FIG. 4 the plug is engaged with the tube and seals the drain port and prevents fluid from dripping from the container after it has been emptied.

The manually operated multipart valve 102 thus dispenses with the need to separate an inlet to the fluid receiving volume from an outlet from the volume. Consequently there is no longer a requirement for an appropriate sealing valve on the inlet, and on the outlet, for an equivalent function can be reliably provided by means of the manually operated valve 102.

Figure 7:
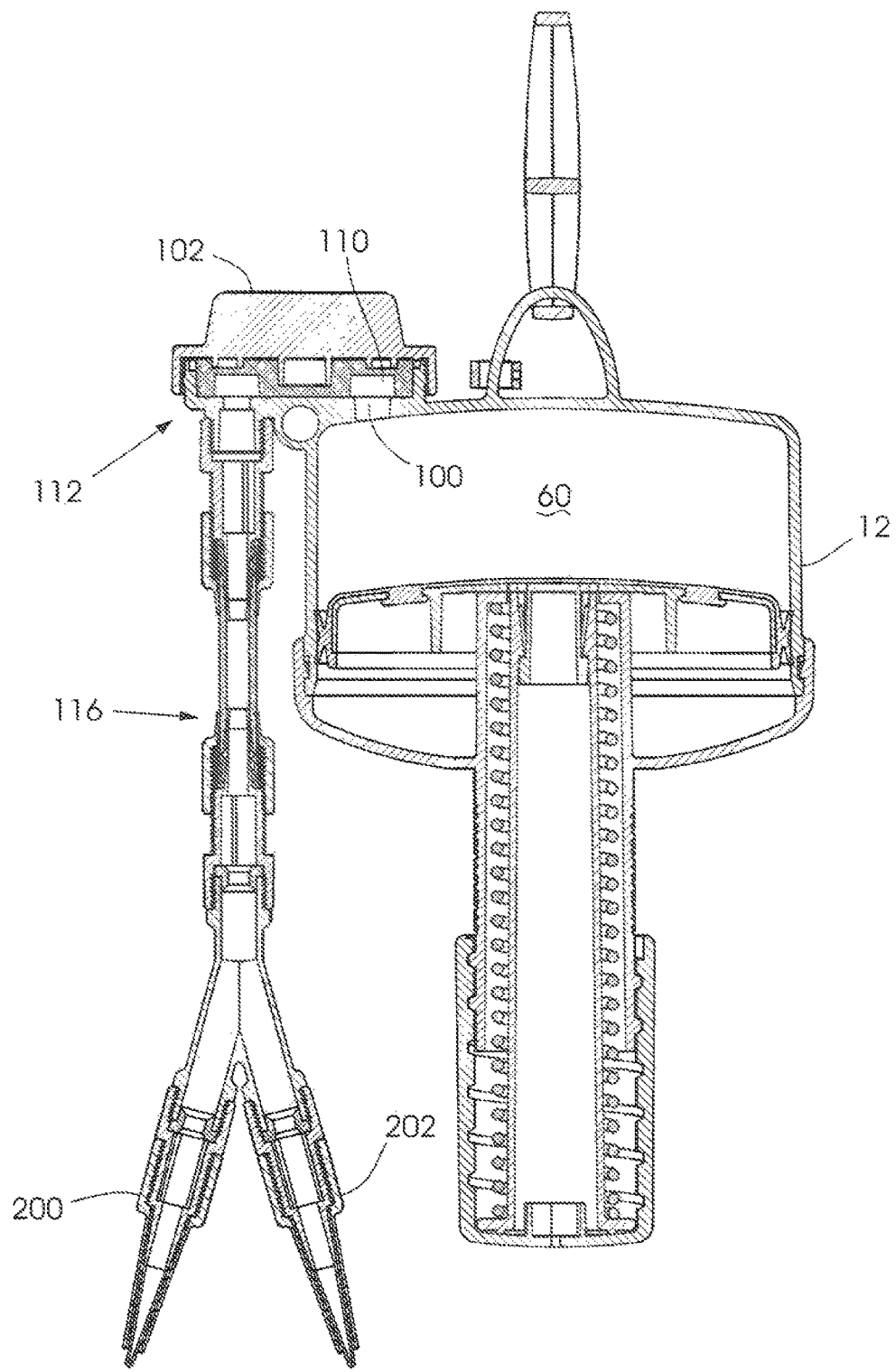
FIG. 7 is a view of the drainage device in cross-section from one side taken on a line 7-7 in FIG. 6.
Figure 8:
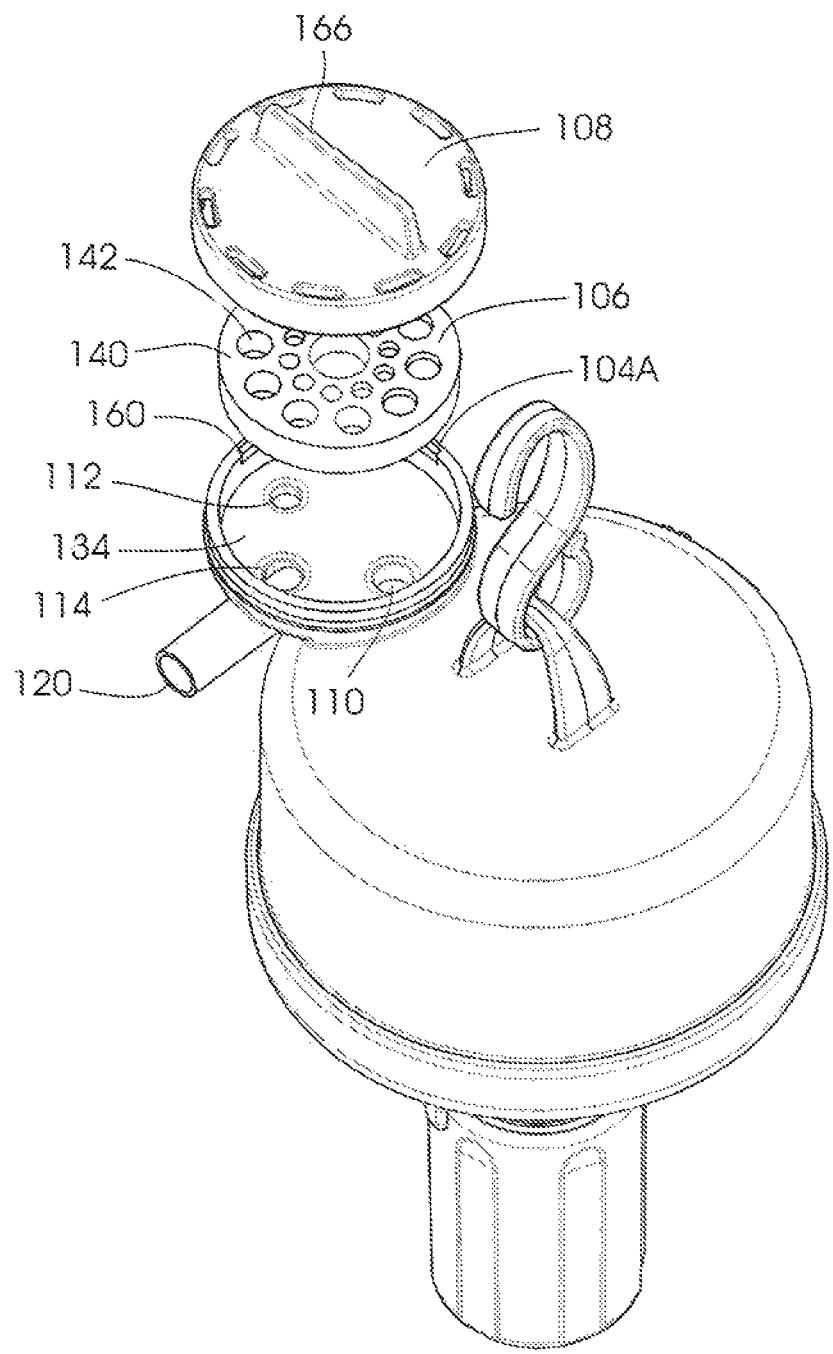
FIG. 8 is a perspective view from above of the drainage device of FIG. 5 showing the valve in an exploded configuration.
Figure 9:
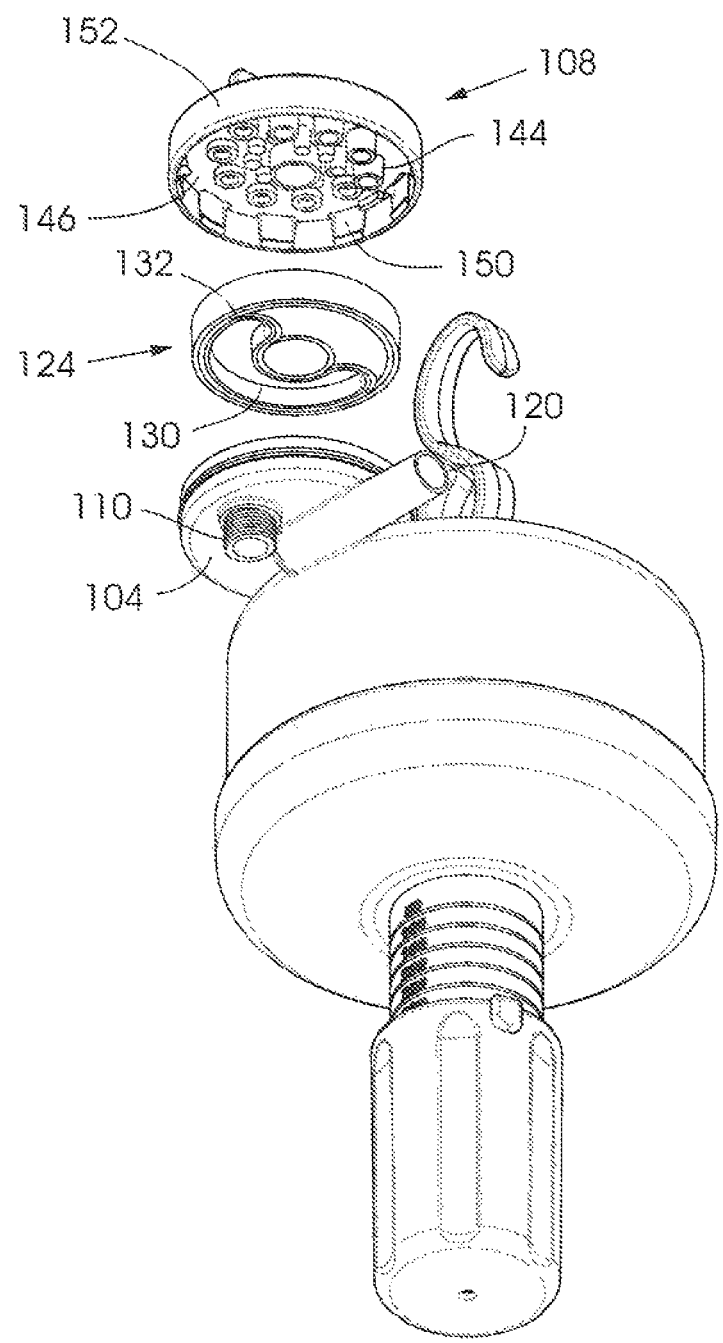
FIG. 9 is a perspective view, from below, of the arrangement of FIG. 8.
Figures 12, 13:
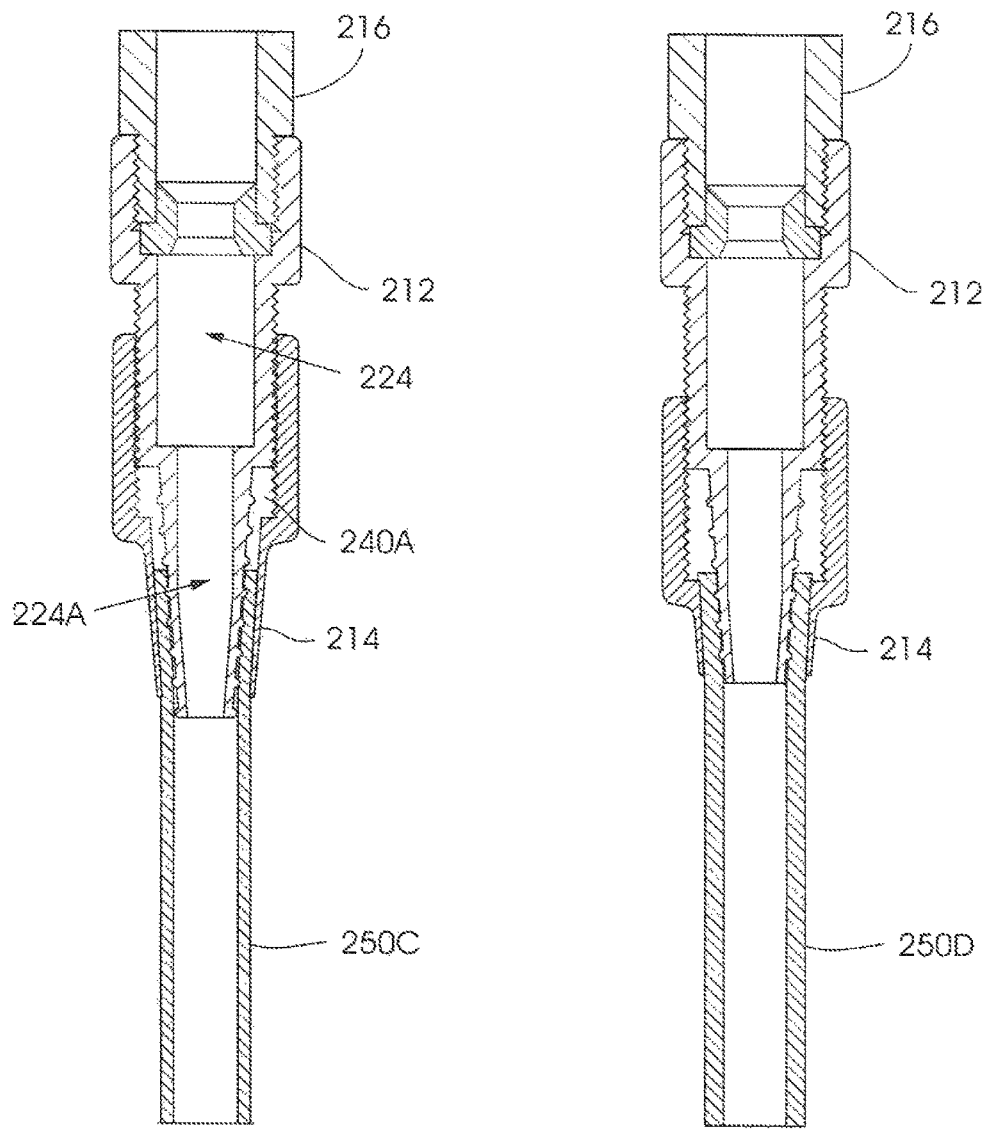

FIGS. 4, 5 and 7 also illustrate two substantially identical connectors 200 and 202 respectively at an end of the drainage tube 116. Two drainage tubes 200A and 202A, shown in dotted outline, are coupled to the connectors 200 and 202 respectively and extend to locations on a wound (not shown) from which fluid is to be drained. As indicated in the preamble hereof in many instances the tubes 200A and 202A are provided, by different supplies, various diameters. The coupling of tubes of different diameters to the drainage device of the invention can thus be problematic. The connectors 200 and 202 help to a considerable extent to alleviate this problem.

FIG. 10 illustrates from one side and in cross-section the connector 200. The connector 202 is substantially the same as the connector 200 and for this reason only the connector 200 is described.

The connector 200 includes a first tubular member 212 and a second tubular member 214.

The first tubular member 212 is connected to tubular structure 216 in any appropriate way. The tubular structure may be a tube 200A, as shown in FIG. 4, a spigot on a container or the like.

Preferably a seal 218 is provided at an interface between the first tubular member 212 and the tubular structure 216, which enables the connector 200 to be pivoted about a longitudinal axis 220 relative to the tubular structure. This feature adds to the ease of use of the connector.

The first tubular member 212 has a passage 224 which extends through it. The first tubular member consists of a first section 226 and a second section 228. The first section is of constant external cross-sectional circular shape and carries external threads 230. The second section 228 tapers and reduces in external cross-sectional dimension moving away from the first section 226. The size of the passage 224, within the second section, is initially constant but subsequently reduces to accommodate the taper on the external surface.

The second tubular member includes a first part 236 and a second part 238. A passage 240 extends tip rough the second tubular member.

The first part 236 is in the nature of a union nut and, in cross-section, internally constant. A thread 242 on an inner surface is complementary in shape to the thread 230 on the first section and is threadedly engageable therewith.

The second part 238 is tapered moving away from the first part. A portion of the passage 240 within the second part, designated 240A, is tapered and is generally of the same degree of taper as the tapered external surface of the second section 228.

The tubular members are each integrally moulded from a suitable plastics material. The plastics material is fairly tough, yet pliable, and it is possible to cut the second section and the second part with an appropriate tool, such as a sharp pair of scissors with relative ease.

FIGS. 10, 11, 12 and 13 show that the connector can be used with flexible tubing 250A, 250B, 250C and 250D respectively of substantially different internal and external diameters. By way of example only the following table sets out the internal and external diameters of the tubes:

| 250A | 250B | 250C | 250D |
|---|---|---|---|
| Internal: 2.1 mm | Internal: 3.2 mm | Internal: 4.3 mm | Internal: 5 mm |
| External: 3.5 mm | External: 5 mm | External: 6.5 mm | External: 8 mm |

Although the dimensions given are exemplary only, the variation in the internal diameter is over 100% and this is the case with the external diameter as well.

In each instance the second tubular member is disengaged from the first tubular member. In the FIG. 10 embodiment, the relatively small diameter tube 250A is pushed through a lower mouth of the first part and then onto the tapered external surface of the second section. The first part is then threadedly engaged with the first section and as the threaded coupling of these components is increased the tapered inner surface of the second part is drawn over the outer surface of the tube and, in the process, the tube is clamped in position in a gap 252 between the second part and the second section.

FIG. 11 shows that if a tube 250B has larger dimensions, lengths 260 of the second part and of the second section are severed from the respective tubular elements beforehand. Otherwise the process is the same as what has been described. A similar technique is adopted as the size of the tube further increased — these situations are shown for the tube 250C in FIG. 12 and for the tube 250D in FIG. 13

It is necessary to shorten the lengths of the tapered elements of the first tubular member and of the second tubular member to accommodate the differently sized tubes. This is easily done with a sharp pair of scissors. If the tube which is be coupled to the connector has a large internal diameter then little is to be gained by threading the tube over the tapered external surface of the second section. All that is required is to urge the tube into frictional engagement with part of the tapered external surface of the second section and, for ease of use, a part of the second section which does not frictionally engage with the inner surface of the tube is severed and discarded. On the other hand, with the second part of the second tubular member a portion of the second tubular member is severed to expose a portion of the bore which has an adequate diameter to allow the tube to pass there through with relative ease.

A significant benefit of the connector lies in its capability to couple tubes of different diameters to the drainage device. It is necessary to cut the members as appropriate but this requirement is of a minor nature. Another benefit lies in the fact that the tubular members are threadedly interengaged with one another and in the process a portion of the tube between opposing surfaces of the tubular members gripped with a tight clamping force. This force is such that it would not normally be possible for the tube to be inadvertently detached from the connector.

The invention claimed is:

1. A fluid drainage device (10; 10A; 10B) for use in a closed wound drainage system, the device comprising:
 a body (12), with a cylindrical bore (26) which defines at least part of a fluid-receiving volume (60),
 an inlet (16) to the fluid-receiving volume (60), a piston (28), in sealing contact with the bore (26), which partly bounds the fluid-receiving volume (60), the piston (28) being movable between a first position and a second position against a friction force between the bore and the piston, a piston rod (32) which extends from the piston (28), an energy storage device (34) which exerts a piston moving force on the piston, a user-actuated handle mechanism (14) which is movable relative to the body in a first direction, to allow the piston (28) to move from the first position at which maximum energy is stored in the energy storage device (34) to the second position at which the energy stored in the energy storage device (34) is reduced, wherein as the piston (28) moves automatically from the first position to the second position, the size of the fluid receiving volume (60) is increased establishing a vacuum level in the fluid receiving volume (60) whereby fluid is caused to flow through the inlet (16), into the fluid-receiving volume (60), and wherein the friction force reduces from a maximum value with the piston at the first position to a minimum value with the piston at the second position thereby to minimise a change in the vacuum level as the piston moves from the first position to the second position so that fluid flow into the fluid receiving volume takes place at a substantially constant rate as the piston moves from the first position into the second position.

2. The device (10; 10A; 10B) according to claim 1 wherein the handle mechanism (14) includes an inner tubular member (36) which is externally threaded and in which the piston rod (32) and energy storage device (34) are at least partly housed and an outer tubular member (38) which is threadedly engaged with the inner tubular member (36) such that rotation of the outer tubular member (38) in a first direction causes the outer tubular member (38) to move linearly along the inner tubular member (36), causing the energy storage device (34) to release energy, thereby creating a region of reduced pressure in the volume (60) and causing or allowing the piston (28) to move towards the second position.

3. The device (10A) according to claim 2 wherein the shape of the bore (26) is varied so that the friction force reduces as the piston moves from the first position to the second position.

4. The device (10A) according to claim 3 wherein the cross-sectional area of the bore (26) is increased from one end (26X) of the bore to an opposing end (26Y).

5. The device (10B) according to claim 4 which includes a valve (102) connected to the inlet (16; 100), which has an inlet port (112) and a drain port (114) and which is operable to connect the inlet port (112) to the inlet (16; 100) and hence to the fluid receiving volume (60), so that the device can act in a drainage mode or, alternatively the valve (102) is operable to connect the drain port (114) to the inlet (16; 100) so that fluid from the fluid receiving volume (60) can be expelled to waste.

6. The device (10; 10A; 10B) according to claim 4 which includes a connector (200) which is connected to the inlet (16; 100) and which includes a first tubular member (212) with a first section (226) of constant external circular cross-section which is externally threaded and a second section (228) which extends from the first section (226) and which is tapered reducing in external size away from the first section (226), and a second tubular member (214) with a passage (240), the second tubular member having i) a first part (236) where the passage has a constant cross-sectional area and is internally threaded so that the first part (236) is threadedly engageable with the first section (226), and ii) a second part (238) which encloses a length (240A) of the passage which is tapered reducing in cross-sectional area moving away from the first part (236).

7. The device (10B) according to claim 3 which includes a valve (102) connected to the inlet (16; 100), which has an inlet port (112) and a drain port (114) and which is operable to connect the inlet port (112) to the inlet (16; 100) and hence to the fluid receiving volume (60), so that the device can act in a drainage mode or, alternatively the valve (102) is operable to connect the drain port (114) to the inlet (16; 100) so that fluid from the fluid receiving volume (60) can be expelled to waste.

8. The device (10; 10A; 10B) according to claim 3 which includes a connector (200) which is connected to the inlet (16; 100) and which includes a first tubular member (212) with a first section (226) of constant external circular cross-section which is externally threaded and a second section (228) which extends from the first section (226) and which is tapered reducing in external size away from the first section (226), and a second tubular member (214) with a passage (240), the second tubular member having i) a first part (236) where the passage has a constant cross-sectional area and is internally threaded so that the first part (236) is threadedly engageable with the first section (226), and ii) a second part (238) which encloses a length (240A) of the passage which is tapered reducing in cross-sectional area moving away from the first part (236).

9. The device (10B) according to claim 2 which includes a valve (102) connected to the inlet (16; 100), which has an inlet port (112) and a drain port (114) and which is operable to connect the inlet port (112) to the inlet (16; 100) and hence to the fluid receiving volume (60), so that the device can act in a drainage mode or, alternatively the valve (102) is operable to connect the drain port (114) to the inlet (16; 100) so that fluid from the fluid receiving volume (60) can be expelled to waste.

10. The device (10; 10A; 10B) according to claim 2 which includes a connector (200) which is connected to the inlet (16; 100) and which includes a first tubular member (212) with a first section (226) of constant external circular cross-section which is externally threaded and a second section (228) which extends from the first section (226) and which is tapered reducing in external size away from the first section (226), and a second tubular member (214) with a passage (240), the second tubular member having i) a first part (236) where the passage has a constant cross-sectional area and is internally threaded so that the first part (236) is threadedly engageable with the first section (226), and ii) a second part (238) which encloses a length (240A) of the passage which is tapered reducing in cross-sectional area moving away from the first part (236).

11. The device (10B) according to claim 1 which includes a valve (102) connected to the inlet (16; 100), which has an inlet port (112) and a drain port (114) and which is operable to connect the inlet port (112) to the inlet (16; 100) and hence to the fluid receiving volume (60), so that the device can act in a drainage mode or, alternatively the valve (102) is operable to connect the drain port (114) to the inlet (16; 100) so that fluid from the fluid receiving volume (60) can be expelled to waste.

12. The device (10; 10A; 10B) according to claim 11 which includes a connector (200) which is connected to the inlet (16; 100) and which includes a first tubular member (212) with a first section (226) of constant external circular cross-section which is externally threaded and a second section (228) which extends from the first section (226) and which is tapered reducing in external size away from the first section (226), and a second tubular member (214) with a passage (240), the second tubular member having i) a first part (236) where the passage has a constant cross-sectional area and is internally threaded so that the first part (236) is threadedly engageable with the first section (226), and ii) a second part (238) which encloses a length (240A) of the passage which is tapered reducing in cross-sectional area moving away from the first part (236).

13. The device (10; 10A; 10B) according to claim 1 which includes a connector (200) which is connected to the inlet (16; 100) and which includes a first tubular member (212) with a first section (226) of constant external circular cross-section which is externally threaded and a second section (228) which extends from the first section (226) and which is tapered reducing in external size away from the first section (226), and a second tubular member (214) with a passage (240), the second tubular member having i) a first part (236) where the passage has a constant cross-sectional area and is internally threaded so that the first part (236) is threadedly engageable with the first section (226), and ii) a second part (238) which encloses a length (240A) of the passage which is tapered reducing in cross-sectional area moving away from the first part (236).

14. The device (10; 10A; 10B) according to claim 13 wherein, with the tubular members (212; 214) interengaged a gap is formed between opposing surfaces of the second section (228) and of the second part (238) and wherein part of a flexible tube is located in the gap and is clamped to the connector (200).

15. The device according to claim 1, wherein,
the bore is tapered from a top of the body to a bottom of the body and has a cross-section dimension that increases from the top of the body to the bottom of the body, the bore being tapered causing the friction force between the piston and the bore to be a variable friction force that is exerted throughout the movement of the piston in the bore from the first position to the second position, the frictional force reducing from a maximum to a minimum as the piston moves from the first position to the second position.

16. The device according to claim 1, wherein,
the user-actuated handle mechanism (14) is located at a lower end of the body (12),
the inlet (16) being a fluid inlet and being located in an upper end of the body, the inlet (16) having a connection for an elongate flexible drainage conduit (90),
the energy storage device (34) is a spring extending around and along a length of the piston rod (32), the spring and the piston rod being housed within the handle mechanism (14),
the spring exerts the piston moving force on the piston between the first position and the second position against the friction force, and
the friction force is exerted throughout the movement of the piston in the bore from the first position to the second position, the friction force reducing from a maximum to a minimum as the piston moves from the first position to the second position.

\* \* \* \* \*